(12) United States Patent
Hu (10) Patent No.: US 10,828,397 B2
(45) Date of Patent: Nov. 10, 2020

(54) REGENERATIVE MEDICAL MATERIAL, PREPARATION METHOD THEREFOR, AND USE THEREOF

(71) Applicant: Fang Hu, Dazhu County (CN)

(72) Inventor: Fang Hu, Dazhu County (CN)

( * ) Notice: Subject to any disclaimer, the term of this patent is extended or adjusted under 35 U.S.C. 154(b) by 31 days.

(21) Appl. No.: 16/327,734

(22) PCT Filed: Aug. 24, 2016

(86) PCT No.: PCT/CN2016/096604
§ 371 (c)(1),
(2) Date: May 17, 2019

(87) PCT Pub. No.: WO2018/035773
PCT Pub. Date: Mar. 1, 2018

(65) Prior Publication Data
US 2019/0262505 A1    Aug. 29, 2019

(51) Int. Cl.
| | | |
|---|---|---|
| *A61L 27/44* | (2006.01) | |
| *A61P 17/02* | (2006.01) | |
| *A61K 8/24* | (2006.01) | |
| *A61K 8/25* | (2006.01) | |
| *A61K 8/34* | (2006.01) | |
| *A61K 8/73* | (2006.01) | |
| *A61L 27/12* | (2006.01) | |
| *A61L 27/20* | (2006.01) | |
| *A61L 27/50* | (2006.01) | |
| *A61L 27/52* | (2006.01) | |
| *A61L 27/54* | (2006.01) | |
| *A61L 27/56* | (2006.01) | |
| *A61L 27/58* | (2006.01) | |
| *A61Q 11/00* | (2006.01) | |
| *A61L 27/02* | (2006.01) | |
| *A61K 8/19* | (2006.01) | |

(52) U.S. Cl.
CPC ............... *A61L 27/44* (2013.01); *A61K 8/19* (2013.01); *A61K 8/24* (2013.01); *A61K 8/25* (2013.01); *A61K 8/34* (2013.01); *A61K 8/73* (2013.01); *A61L 27/02* (2013.01); *A61L 27/12* (2013.01); *A61L 27/20* (2013.01); *A61L 27/505* (2013.01); *A61L 27/52* (2013.01); *A61L 27/54* (2013.01); *A61L 27/56* (2013.01); *A61L 27/58* (2013.01); *A61P 17/02* (2018.01); *A61Q 11/00* (2013.01)

(58) Field of Classification Search
CPC ........ A61L 27/12; A61L 27/52; A61L 27/505; A61L 27/58; A61L 27/44; A61L 27/54; A61L 27/02; A61L 27/20; A61L 27/10; A61L 27/56; A61L 2430/34; A61L 2430/02; A61K 8/19; A61K 8/24; A61K 8/73; A61K 8/25; A61P 17/02; A61Q 11/00
See application file for complete search history.

(56) References Cited

FOREIGN PATENT DOCUMENTS

| | | |
|---|---|---|
| CN | 101401964 A | 4/2009 |
| CN | 103086708 A | 5/2013 |
| CN | 104043150 A | 9/2014 |
| CN | 104888281 A | 9/2015 |
| CN | 105169458 A | 12/2015 |
| CN | 106421889 A | 2/2017 |

OTHER PUBLICATIONS

Baino et al., "Robocasting of Bioactive SiO2-P2O5-CaO-MgO-Na2O-K2O Glass Scaffolds" in Journal of Healthcare Engineering, vol. 2019, pp. 1-13.*
Zhang, X-K et al. "Mophology Character of the Sol-gel Derived Bioactive Glass in SBF Solution" Chinese Journal of Chemical Physics, 2004, 17(4), 496.

* cited by examiner

*Primary Examiner* — Blessing M Fubara
(74) *Attorney, Agent, or Firm* — MT Law LLC; Meng Yan (57) ABSTRACT

Disclosed are a regenerative medical material for promoting the repair of soft and hard tissues, a preparation method therefor, and the use thereof. The regenerative medical material has a three-dimensional network structure and is a composite material composed of inorganics and organics, wherein the mass ratio of the inorganics to the organics is 2:1-4:1. Based on the total mass of the inorganics, the inorganics contain 12-38% $SiO_2$, 3-5% $Na_2O$, 15-29% CaO, 10-32.5% $P_2O_5$, 1-5% inositol hexaphosphate, 1-5% cyclohexanhexol phosphate, and the balance of impurities, with the content of impurities being less than 0.5%. Based on the total mass of the organics, the organics contain 30-60% carboxymethyl chitosan and 30-60% sodium hyaluronate. The regenerative medical material has a composition and properties better suited to the human body and plays a key role in cell repair and bonding, cell proliferation, and promoting the growth of hair follicles.

12 Claims, 10 Drawing Sheets

REGENERATIVE MEDICAL MATERIAL, PREPARATION METHOD THEREFOR, AND USE THEREOF

FIELD OF THE INVENTION

The present invention relates to the regenerative medical area, specifically relates to a regenerative medical material, the preparation method thereof and the application thereof.

BACKGROUND OF THE INVENTION

The most prominent features of the biological active glass and glass ceramic are the surface condition varies dynamically as time goes on after they are implanted into the human body and carbonate hydroxyapatite (HCA) layer is formed on their surfaces which provides bonding interface for the tissue. As most of biological active glasses are type A biological active materials, being either osteoproductive or osteoconductive function, which present excellent bondability with bones and soft tissues, biological active glasses (BAG) are deemed to be excellent biological materials that can be applied in the repair field. This kind of restorative material not only have extremely wide uses but also presents irreplaceable magic efficacy in professional products of multiple areas such as skin care, whitening and wrinkles, burns and scalds, mouth ulcers, gastrointestinal ulcers and skin ulceration, killing fungi, bone repair, bonding of soft tissue and bone tissue, etc., its appearance will make outstanding contribution to the human health. Besides, BAG also has a fast surface reaction, amorphous two dimensional structure makes the strength and fracture toughness low, and elastic modulus (30-35 MPa) is low which is close to that of the cortical bone. The machinable biological glasses are of excellent processing property.

However, this kind of biological glasses presents some key issue such as: 1. complete degradation thereof usually takes 1 to 2 years as the degradation rate is slow; 2. the pH value is unstable and can reach to 11, forming a strong alkaline and presenting certain cytotoxicity; 3. the reaction temperature of this kind of biological glasses is high as adopting melting quenching reaction, being 1700-1900° C., which causes high energy consumption, and the investment for the construction of a standard manufacturing line requires over one billion; 4. This kind of biological glasses cannot form porous materials, making it difficult to achieve the highly compliance and extending functions of the material.

Therefore, there is an urgent need for a novel regenerative medical material that can replace the above-mentioned biological glasses in the market at present.

DESCRIPTION OF THE INVENTION

In order to solve the above-mentioned technical problem, one aspect of the present invention provides a regenerative medical material for promoting the repair of soft and hard tissues. The regenerative medical material has a three-dimensional network structure and is composite material consisting of inorganics and organics, wherein the mass ratio of the inorganic to the organics is 2:1-4:1.

Based on the total mass of the inorganics, the inorganics comprises 12-38%$SiO_2$, 3-5% $Na_2O$, 15-29% CaO, 10-32.5% $P_2O_5$, 1-5%inositol hexaphosphate, and 1-5%cyclohexanhexol phosphate, and the balance of impurities, with the content of impurities being less than 0.5%.

The organics contains 30-60% carboxymethyl chitosan and 30-60% sodium hyaluronate based on the total mass of the organics.

In a preferred embodiment, the mass ratio of the inorganics to the organics is 3:1. Besides, the weight ratio of calcium to phosphorus in the inorganics is 1.5 to 1.8, preferable 1.67. In a preferred embodiment, a pH value of the regenerative medical material for promoting the repair of soft and hard tissues is 7.4±1. In a preferred embodiment, a degradation time of the regenerative medical material for promoting the repair of soft and hard tissues in vivo is 4 weeks to 12 weeks. In a preferred embodiment, a method of preparing the regenerative medical material for promoting the repair of soft and hard tissues comprises the following steps:

mixing soybean extract used as a phosphorus precursor, ethyl orthosilicate used as a silicon precursor, at least one of calcium nitrate tetrahydrate, calcium nitrate and calcium chloride used as a calcium precursor and water and/or ethanol used as reaction medium to prepare a gelatin precursor sol solution, and sintering the gelatin precursor sol solution at a constant temperature of 300~700° C. to obtain inorganics; mixing the inorganics with carboxymethyl chitosan and sodium hyaluronate, and heating to dissolve; wherein the preparation method of the soybean extract comprises: (1) smashing a soybean hull; (2) acid leaching a smashed material and filtering; (3) neutralizing a leach liquor with alkali; (4) precipitating and leaching a calcium salt (5) ion exchanging with RH+ resin; (6) evaporating and concentrating to obtain the soybean extract, wherein the content of hydroxyl phosphorus in the soybean extract is 40-60 mass %.

In a preferred embodiment, the inorganics is obtained through the sol-gelatin method by adopting the soybean hull extract as the phosphorus precursor and sintering at a constant temperature of 300~700° C.

The another aspect of the present invention provides a cell growth carrier comprising the above-mentioned generative medical material for promoting the repair of soft and hard tissues. Preferably, the cell growth carrier is a medical device, and especially is at least one part of the implants.

Still another aspect of the present invention provides a method for promoting the repair of soft and hard tissues, in which the regenerative medical material mentioned in the present invention is used.

Other aspects of the present invention provide the use of the mentioned regenerative medical material for promoting the repair of soft and hard tissues in preparing the pharmaceutical composition, medical device, oral care product, orthopedic product or cosmetic.

The regenerative medical material in the present invention can better control the degradation rate of the materials to make the degradation rate of original biological active glasses controllable, which synchronizes the degradation rate of the new bone implant material in the artificial bone material application field and overcome the phenomenon that the newborn bone cannot realize the triple repair of bone structure, shape and function. When used in the aspects such as the repair for bone, spinal and bone defects and oral bone implant, etc, the regenerative medical material in the present invention is of great significance.

In the present invention, the introduction of phosphorus by the soybean extract can increase the degradation rate of the regenerative medical material. Biological active components range of the material prepared by the traditional method is small, and the degradation rate is usually restricted by decreasing the content of phosphorus. Phosphoric acid and ethyl phosphate etc, commonly being used in the material prepared by the original traditional method, which has poor compatibility with calcium precursor (such as calcium nitrate) and is prone to cause the precipitation and separation. The selection of glycol with great toxicity will decrease the concentration of the precursor, a great amount of energy and time will be consumed during such process of processing solvent and it is very hard to realize the standardized and scale production.

The phosphorus precursor in the present invention can be effectively consoluted with calcium precursors such as calcium nitrate, the solvent is water, ethanol or the mixture thereof. As the toxicity is small and asolvent-removing temperature is low, by changing precursors such as calcium and sodium etc to fulfill forming gelatin at room temperature, and the physiochemical indexes of the biological active glasses can be reached within 600° C. It overcomes the defects in the traditional method and realizes the standardized and scale production.

In the regenerative medical material of the present invention, 1% to 10% silicon atoms possess a high coordination number of over 5 and these high-coordination silicons are formed under common pressure. High-coordination silicons have certain influence on the structure and properties of the materials. For example, high-coordination silicons will cause the absorption peak of ultraviolet rays to transfer.

In the solution synthesis, most high-coordination silicons mainly coordinates with N, F or Cl but rarely with O at present. By changing the external stimuli such as the temperature, solvent and irradiation intensity, the coordination number of silicon atoms can be changed, the increase of temperature will make the 5-coordinate silicon increase and 5-coordinate silicon and 6-coordinate silicon can transform mutually under the irradiation. The introduction of polyol helps to improve the formation probability of high-coordination silicon for polyol can facilitate the coordination of oxygen and silicon atom so as to form the high-coordination silicon. For the high-coordination silicon, generally the treatment of glasses at high temperature will allow the coordination number of silicon to change from 4 to 6, after which it mainly exits in the form of Si—O—P or Si—O—Si. The number of 6-coordinate silicon will increase as the content of phosphorus increases and the glass material will crystallize after heat treatment. However, solid materials of silicon which contain high-coordination silicon atoms at middle and low temperature and common pressure do not occur in researches at present.

The regenerative medical material in the present invention is superior to the biological active glasses in the physical and chemical indicators and biological indicators. During the production of this material, a scale production which is energy saving at a low temperature of 600° C. and presents a controllable quality is realized, and the defects such as high energy consumption, low product pass rate in the original calcination at 1700~1900° C. are changed. Under the condition of adopting this regenerative medical material as the parent, the addition of other medical materials into it will realize its wide applications in the biological therapeutical area.

Preferably, the ratio of the calcium to phosphorus in the regenerative medical material of the present invention is relatively the same with that in human bones, for example it is about 1.67. The formed three dimensional reticular structure and holes diameter can be consistent with the holes diameter of human bones and soft tissues. The biological activity, stability and degradation rate of the materials are realized to be controllable. This material has a low preparation temperature and can load the biological active molecules such as protein, antibiotics and chemotherapeutical agents. The material has porosity and can be used in the drug loading and controlled release. Meanwhile, the selected phosphorus precursor is a natural material with an extremely small toxicity relative to the traditional phosphorus precursor, so as to improve the biological compatibility of the material. The material quickly forms hydroxylapatite on its surface in the simulated body fluid (SBF). This material can overcome the problem of poor plasticity in the traditional biological active glasses. The adjustable amorphous material with an amorphous structure is formed. Compared to that other biological active glasses are basically crystals, the regenerative medical material in the present invention is non-crystals, which has an uniform particles, stable biological compatibility, excellent dispersibility and strong stability. It is completely controllable to realize the compression strength and degradation rate in human bones.

The regenerative medical material in the present invention contains ions such as Si, Ca, Na and P and the ratio of each ion is the same with that of ions in the human bones tissue. These ions are uniformly distributed in the multiholes of $SiO_2$ calcinated at high temperature, naturally allowing the material to react with the body fluid by eight steps of surface reaction.

First step: $Na^+$ and $K^+$ ions in the material are uniformly distributed in the multiholes of $SiO_2$ (the hole diameter thereof is almost the same with that in the human bones), they quickly exchanges with $H^+$ and $H_3O^+$ ions after contacting with the body fluid, which can be exemplified by:

Wherein, $OH^-$ is negative charge, which adsorbs the matters such as bone tissue and soft tissue cells, growth factors and collagen etc into the holes to grow orderly and form the growth organic block (new tissue) of human body structures. Make the regenerative cells gene express and grow orderly, and form the osteoconductive and osteoacusis ability.

Second step: Si—O—Si bond is broken by the solution and multiple Si—OH are formed outside of the interface.

Third step: the polymerization reaction of Si—OH will form the porous limb layer of $SiO_2$, which binds to different kinds of proteins through a hydrogen bond and an ionic amine bond (—Si—O—$H_3N^+$—) to form protein absorption of high density and the silicon sol layer as well as the carbonate hydroxyapatite layer. As the hydroxyapatite layer possesses a large surface area, it is suitable for absorbing massive biological molecules so as to facilitate the extracellular response. Compared with silicon sol layer with lower quantity of negative charges, the new bones absorb more biological molecules.

Fourth step: high coordination silicon atom 6 and silicon atom 4 exchange with potassium ions in human body to form a stable three dimensional reticular solid mechanism, changing the original silicon atoms to be free state. And it can naturally exchange with the chemical ingredients in the human body to form a carrier of creeping substitution and the high coordination silicon will allow the absorption peak of the ultraviolet to transfer, which plays the role of anti-oxidation.

Fifth step: $Ca^{2+}$ and $PO_4^{3-}$ are originated from materials or solution and collect on the $SiO_2$ rich limb layer and then form $CaO$—$P_2O_5$ amorphous phase layer; by adjusting the ratio of phosphorus, the degradations of newborn cells can be regulated to synchronize with the degradations of original implants.

Sixth step: as the $OH^-$ and $CO_3^{2-}$ educing from the solution, $CaO$—$P_2O_5$ astatic phase layer can be transformed into hydroxyapatite (HCA) polycrystal containing carbon, which is absorbed on the surface of the trauma, ulcer and soft tissue and then play role of facilitating cell proliferation, facilitating the healing of trauma and seamless wound repair.

Seventh step: facilitating the cell proliferation and orderly growth, facilitating the formation of hair follicle and the growth of hair follicle, and reaching the effect of reducing scars.

Eighth step: ulcer wound, especially the oral ulcer and cervical erosion are both caused by anaerobic bacteria. The regenerative medical material in the present invention can form a weak alkali environment to make the anaerobic bacteria die from dehydration and meanwhile inhibit the growth of the anaerobic bacteria and facilitate the repair and proliferation of newborn cells.

In summary, the regenerative medical material in the present invention not only has various properties that fit for human bodies but also present a more consistent component and content relationship with that in human bodies so as to be more suitable for the tissue repair.

DETAILED DESCRIPTION OF THE EMBODIMENTS

Now various exemplary embodiments of the present invention will be described in detail and this detailed description shall not be deemed as the limitation to the present invention, but should be understood as a more detailed description on some aspects, properties and embodiments of the present invention.

It should be understood that the terms mentioned in the present invention are merely used to describe particular embodiments rather than to limit the present invention. Besides, for the numerical ranges in the present invention, it should be understood that it further discloses each medium value between the upper and lower limit of the range. Any stated value or an intermediate value within the stated range and any other stated value or each smaller range between the intermediate values within the range are included in the present invention. The upper limit and lower limit of these smaller ranges can independently included or excluded from the range.

Unless otherwise specified, all technical and scientific terms used in the present text have the same meanings as those commonly appreciated by a person skilled in the art. Although the present invention merely describes the preferable materials and applications, any materials that are similar or equivalent to those in the present text can also be used in the embodiments or tests of the present invention. All literatures mentioned in the present specification are incorporated by reference to disclose and describe the methods and/or materials related to the literatures. If there is a conflict with any incorporated literature, the contents in the present specification shall prevail.

In the present invention, unless otherwise pointed clearly in the context, terms include not only singular forms but also plural forms. "at least one of" or "at least one kind of" in the present invention does not merely refer to the situation of "one" or "one kind" but more importantly it further includes the situation of "plurality" or "a plurality kinds of".

The term "regenerative medical material" in the present invention refers to the inorganic-organic composite materials of three-dimensional grid structure having the function of facilitating the regeneration of soft and hard tissues, and sometimes it is also called Regesi regenerative medical material or Regesi etc. These names have the same meanings in the present invention. Preferably, the mass ratio of the inorganics to the organics in the regenerative medical material is 2:1-4:1. If this mass ratio is smaller than 2:1, then the hardness of the obtained regenerative medical material becomes poor and cannot act as the carrier for cell growth very well. On the other aspect, if this mass ratio is larger than 4:1, then the content of each elements in inorganics is very different from that in human tissues, especially hard tissues such as bones, which is bad for the regeneration of tissues, especially hard tissues. Preferably, the mass ratio of inorganics to organics is 2.5:1-3.8:1, more preferably 2.6:1-3.5:1, further preferably 2.8:1 to 3.4:1, such as 3:1 etc.

In the present invention, on the basis of the total mass of inorganics, the content of $SiO_2$ in the inorganics is 12-38%, preferably 15-35%, more preferably 16-33%, further preferably 18-30%, such as 20%, 25%, 28%, 29% etc. The content of $Na_2O$ in the organics is 3-5%, preferably 3.5-4.5%, more preferably 3.6-4.2%, further preferably 4%. The content of CaO in the inorganics is 15-29%, preferably 16-27%, more preferably 18-25%, further preferably 20-22%. The content of $P_2O_5$ in the inorganics is 10-32.5%, preferably 12-30%, more preferably 14-28%, further preferably 16-26%, still preferably 18-24%, 20-22%. The content of inositol hexaphosphate in the present invention is 1-5%, preferably 2-4%, more preferably 3%. The content of cyclohexanhexol phosphate in the present invention is 1-5%, preferably 2-4%, more preferably 3%. If the content of the above-mentioned each component in the inorganics is too low or too high, the content of each element in the regenerative medical material will be inconsistent with that in organisms such as hard tissues like bones in human bodies, thereby be adverse to facilitate the regeneration or repair of tissues.

Inositol hexaphosphate and cyclohexanhexol phosphate can either be added as independent ingredients or be mixed during the preparation process by being contained in the soybean extract in the present invention.

In the present invention, the components apart from the above-mentioned ones in the inorganics are all impurities inevitably produced during the preparation process in the present invention, as impurities, the content thereof is commonly smaller than 0.5 mass %, preferably smaller than 0.4 mass %, more preferably smaller than 0.2 mass %, especially preferably smaller than 0.1 mass %, most preferably 0.

In the present invention, on the basis of the total mass of the organics, the content of carboxymethyl chitosan in the organics is 30-60%, preferably 40-55%, more preferably 45-50%, further preferably 48%. The content of the sodium hyaluronate in the organics is 30-60%, preferably 40-55%, more preferably 45-50%, further preferably 48%.

In the present invention, preferably, the weight ratio of the calcium to phosphorus in the inorganics is 1.5 to 1.8, preferably 1.67. The ratio of the calcium to phosphorus in the range complies with the ratio of the calcium to phosphorus in the organism such as human body.

What needs to notice is that the content of the components and the ratio among each component in the regenerative medical material in the present invention is prepared according to the content and ratio of each element in hard tissues of human bodies. Due to the difference of human bodies, sexes and age groups, the content of elements in the hard tissues have some difference, the content of each component and the ratio thereof in the regenerative medical material of the present invention also have some difference. However, these contents and ratios cannot go beyond the above-mentioned range as a whole.

For example, for the old aged group, the preferable content and ratio of components can be as follows:

| | |
|---|---|
| $SiO_2$ | 36% |
| $Na_2O$ | 3% |
| CaO | 25% |
| $P_2O_5$ | 28% |
| inositol hexaphosphate | 4% |
| cyclohexanhexol phosphate | 4% |

On the basis of the total mass of the inorganics.

| | |
|---|---|
| carboxymethyl chitosan | 50% |
| sodium hyaluronate | 50% |

On the basis of the total weight of the organics.

As for the old aged group, the preferable mass ratio of the calcium to phosphorus is 1.67.

For youngster group, the preferable content and ratio of components can be adaptively adjusted.

In the preparation method of the regenerative medical material for promoting the repair of soft and hard tissues in the present invention, the specific plant extract should be selected so as to realize the beneficial technical effect of the regenerative medical material in the present invention, such as the low pH value which is lower to 7.4 and the controlled release of P (phosphor). The plant extract in the present invention is preferably soybean extract. In some embodiments, the preparation method of the soybean extract comprises: (1) smashing a soybean hull; (2) acid leaching a smashed material and filtering; (3) neutralizing a leach liquor with alkali; (4) precipitating and leaching a calcium salt; (5) ion exchanging with RH+ resin; (6) evaporating and concentrating to obtain the soybean extract, wherein the content of hydroxyl phosphorus in the soybean extract is 40-60 mass %.

Specifically, the preparation steps of the soybean extract in the present invention are as follows:

Taking soybean hull that is smashed and sieved to be about 20 meshes and adding water of 6 times amount thereof into it. Adjusting the pH to 1.5-2 with 7% hydrochloric acid, and stirring and immersing at room temperature. Suction filtering and washing slags with 1.2% hydrochloric acid, discarding the slags and combining the filtrate. Adding the calclime to the leach solution to neutralize pH value to about 6.5 and obtaining the calcium salt precipitation, which is then stood still for 1 hour, conducting the suction filtration, discarding the filtrate and then washing the precipitation with the distilled water for 2-3 times, obtaining the purified calcium salts. Adding a small amount of diluted hydrochloric acid to the obtained calcium salts and adjusting it to the thin slurry, then adding ⅔ times of H type strong acid cation exchange resin thereto. Slightly stirring for 0.5 hour to allow the calcium salt to be dissolved and transformed into soluble salt solution. Suction filtering, washing and separating for the crude liquor extract.

Putting the soluble calcium salt solution obtained by dissolution-transformation into the ion exchange column, and controlling the flow rate to conduct the ion exchange. At this time, impurity ions such as $Mg^{2+}$ and $Ca^{2+}$ in the solution are exchanged onto $RH^+$ resin and the $H^+$ ion is exchanged therefrom. Decoloring with about 1 wt % of active carbon for 1-2 times and separating. Then reducing the pressure of the destaining solution to concentrate and controlling the temperature at about 70-80° C. until the solution within the bottle presents as dilute thickens. Then the soybean extract in the present invention is obtained and the content of the hydroxyl phosphorus needs to be 40-60 wt %.

It is not very clear for the reasons why the plant extract in the present invention can produce and obtain the specific regenerative medical material in the present invention, however it is speculated that it may due to that the compatibility between plant extract and the calcium precursor (such as the calcium nitrate) is enhanced and thus no precipitation is generated. Besides, the plant extract is a natural ingredient without toxicity. The other reason may be that the various other elements contained in the soybean extract interact with other raw materials in the present invention to produce the unexpected effects. Besides, the content composition of each elements in the soybean extract is similar to that of each element in human bodies and the regenerative medical material similar to organisms in composition can be easily obtained.

Besides, the plant extract possesses various components that allow the material to possess three dimensional structure and the various components interact with each other so as to realize the target of preparing the regenerative medical material at low temperature. The defects of traditional methods are overcome and the standardized and scale production are realized.

The silicon precursor and calcium precursor in the present invention can adopt ones commonly used in the present invention. Besides, the water and/or ethanol can be used as the reaction medium in the preparation method in the present invention. In the present invention, the gelatin precursor sol solution prepared from the above-mentioned materials need to be sintered at comparatively low temperature, such as being sintered at a constant temperature of 300~700° C., the temperature can also be preferably 400~600° C., such as 500° C. etc.

In the present invention, the "cell growth carrier" refers to the matrix suitable for the cells, including but not limited to the bone cells and dermal cells, to grow and proliferate. Preferably, the regenerative medical material itself in the present invention can act as carriers directly. Optionally, the regenerative medical material in the present invention is combined/composited with other materials commonly used in the art to act as the carrier.

EMBODIMENTS

The preparation method of the Regesi regenerative medical material

According to the content of the following ingredients, the precursor with the corresponding content is prepared into the gelatin precursor solution (results will not be influenced as changing the calcium nitrate tetrahydrate into calcium chloride or calcium nitrate).

| | |
|---|---|
| $SiO_2$ | 36% |
| $Na_2O$ | 3% |
| CaO | 25% |
| $P_2O_5$ | 28% |
| inositol hexaphosphate | 4% |
| cyclohexanhexol phosphate | 4% |

On the basis of the total mass of the inorganics.

Firstly, 30 ml soybean extract in the present invention is put into a 50 ml sample bottle and then ethyl orthosilicate (TEOS), ethanol and water (the volume ratio is about 1:1 and the amount added therein can be enough to dissolve the above-mentioned precursor) are added therein in turn, it is then stirred for 30 min, during the stirring process, $Ca(NO_3)_2.4H_2O$ (or calcium chloride or calcium nitrate) is added, thereby obtaining the gelatin precursor sol solution. The prepared gelatin precursor sol solution is stood at room temperature until gelling (commonly it needs 2~10 days and it depends on the ratio among each precursors). Then the gelatin is put into an oven at 60° C. for aging over 1 day, it is then put into an oven at 120° C. for baking for 1 week to allow the solvent therein to evaporate entirely and cooled to room temperature. The temperature of the tube furnace is increased from room temperature to 300~400° C at an temperature increasing rate of 5° C./min in the air and the dried gelatin is sintered for at least 10 minutes in the tube furnace at a constant temperature of 300° C.~400° C. and then cooled naturally, thereby obtaining the inorganic powder in the Regesi regenerative medical material.

The carboxymethyl chitosan, sodium hyaluronate and the above-mentioned powder are mixed according to the ratio and then heated to 45 degree centigrade, which is then dissolved and stirred evenly to obtain the mixture. 100 g medicinal glycerol is pre-heated to 80 degree centigrade. Then the above-mentioned mixture is blended into the medicinal glycerol, which is then stirred evenly (the weight ratio of the medicinal glycerol to biological material is 55:45). The mixture is removed with impurities, aged for 24 hours and sterilized with irradiation to obtain the Regesi regenerative medical material in the present invention.

Studies on the Property of the Regesi Regenerative Medical Material

Figure 1:
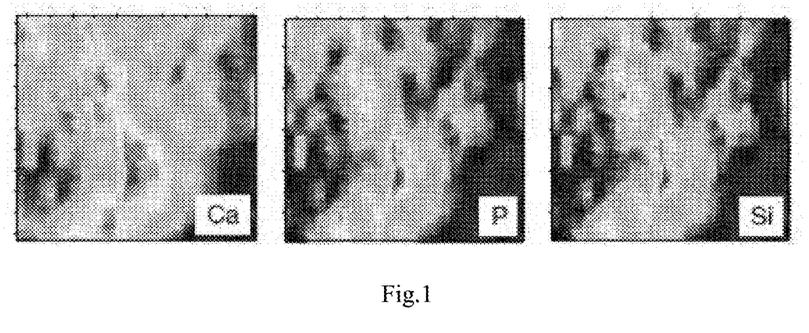
FIG. 1 is the elemental distribution image (210×210 μm²) of the X-ray fluorescence spectrum (XRF) of the exemplary regenerative medical material in the present invention, showing that the chemical components (Ca, P and Si) of the material in the present invention are in an uniform distribution microcosmically.

1. Physical and Chemical Properties:

The chemical composition of materials is analyzed with X-ray fluorescence spectrum (XRF). Researches show that the chemical composition (Ca, P and Si) of the material at the microscale are evenly distributed, as shown in FIG. 1.

Figure 2:
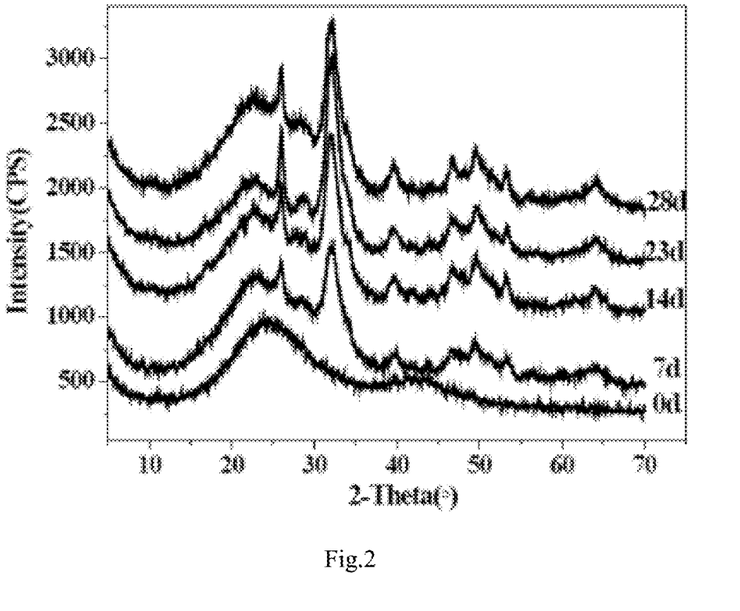
FIG. 2 is the XRD spectrogram for the reaction of the exemplary regenerative medical material in the present invention with the SBF solution at different time.

The Regesi regenerative medical material is immersed into the simulated body fluid (SBF) to conduct the deposition experiment. It is discovered by the research through the X-ray diffraction (XRD) that at depositing for 7 days, diffraction peaks of hydroxylapatite (HA) obviously appear on the surface of the material (as shown in FIG. 2), and diffraction peaks of HA is enhanced as the time goes, indicating that more hydroxylapatites are formed on the surface of the material. After depositing 14 days, the diffraction peak of HA does not change very much, indicating that the formed HA has already covered the surface of the material entirely.

Figure 3:
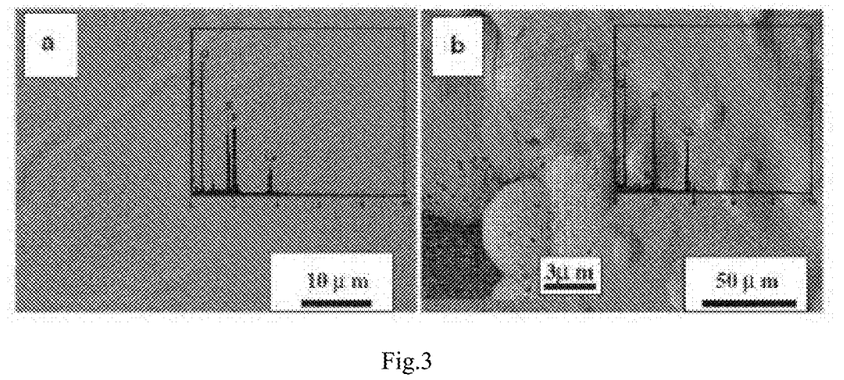
FIG. 3 is SEM-EDXS diagram of the exemplary regenerative medical material in the present invention, wherein a-before the deposition and b-after the deposition with the SBF solution (14 d).

The surface topography of the material is analyzed through the scanning electron microscopy-energy dispersive x-ray energy spectrum (SEM-EDXS), as shown in FIG. 3. The result shows that before depositing in the SBF solution, the surface of the material is flat and EDXS energy spectrum analysis demonstrates that the main components thereof are Si, P and Ca. After depositing 14 days in the SBF solution, spherical particles occur on the surface of the material. It is discovered after magnifying the spherical particles that these particle are made up of acerose HA while it is discovered by the EDXS energy spectrum analysis that the content of Si is decreased and the content of Ca and P (Ca/P~1.65) is increased, further demonstrating the formation of HA. These results are consistent with those from the foregoing XRD.

Figure 4:
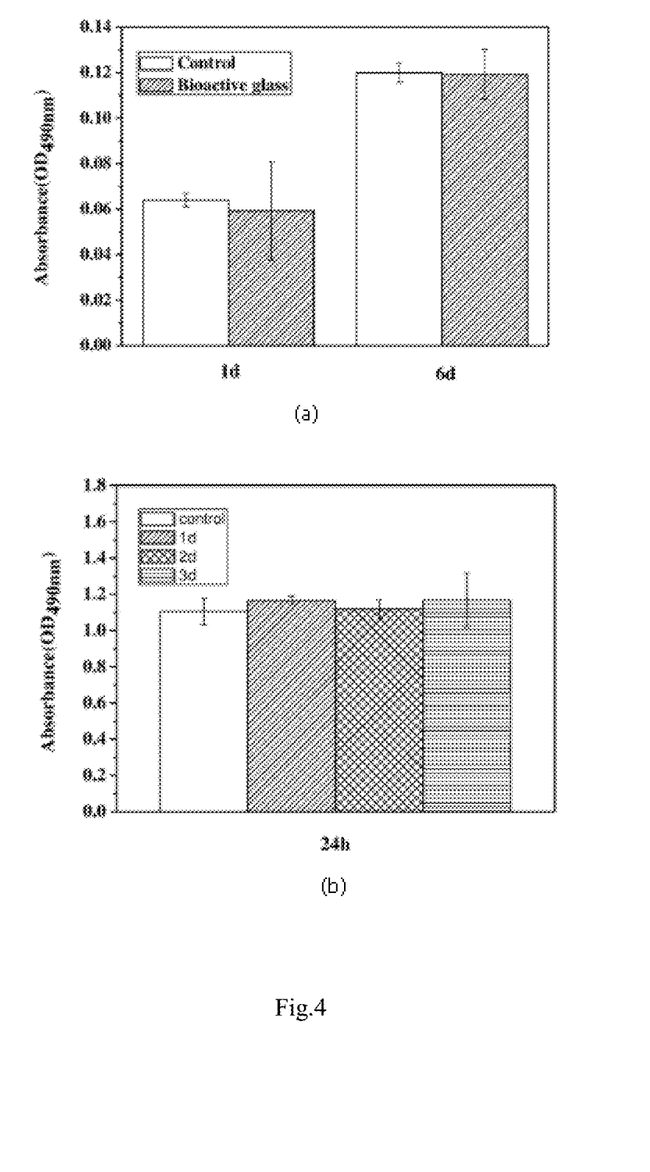
FIG. 4 is MTT values for the interaction of the exemplary regenerative medical material in the present invention and the leaching liquor thereof with the osteoblast, (a) the regenerative medical materials are directly cultured for 1 d and 6 d; (b) Regesi regenerative medical materials are cultured by the leaching solution of different time for 24 hours.

2. Biological Evaluation:

2.1. Cytotoxicity Test:

1% Regesi regenerative medical material powder is directly blended with 10% DMEM/F12 culture solution, and then it is added into 96 hole plate. Preosteoblasts (MC3T3) is inoculated into 96 hole plate under $1\times10^4$ cells/mL, DMEM/F12 culture solution is used as the control group. MTT experiment is conducted after culturing 1 and 6 days in $CO_2$ incubator. After adding MTT, DMSO is added and then vibrating. The absorbance is measured with the enzyme linked immunosorbent assay at 570 nm wavelength, the measurement results are shown in FIG. 4(*a*). The result demonstrates that the Regesi regenerative medical material does not possess cytotoxicity. After culturing for 1 d, the absorbance of the material is slightly lower than that of the blank sample (about 92% thereof), demonstrating that the Regesi regenerative medical material does not possess cytotoxicity. When culturing for 6 days, the absorbance of the material is the same with that of the blank sample, demonstrating that the Regesi regenerative medical material does not have cytotoxicity.

The Regesi regenerative medical material is immersed into the culture solution containing 10% DMEM/F12 by a ratio of 5 mg/ml, and centrifuged after leaching for different periods (1, 2, 3 d) to obtain the supernatant and the 24 hole plate leach liquor is adopted as the blank control group, both of which are stored at 4° C. The pre-osteoblasts (MC3T3) is inoculated into 96 hole plate by $1\times10^4$ cells/mL, and different conditioned leaching liquors are added after culturing in $CO_2$ incubator. After 24 hours, MTT experiments are conducted. After adding MTT, DMSO is added, and then vibrating. The absorbance is measured with enzyme linked immunosorbent assay at 570 nm wavelength, and the measurement results are shown in FIG. 4(*b*). The results show that the absorbance value of the leaching liquors of the Regesi regenerative medical material at different times are substantially the same with that of the blank sample, showing that the leaching liquors of the Regesi regenerative medical material still does not have cytotoxicity.

Figure 5:
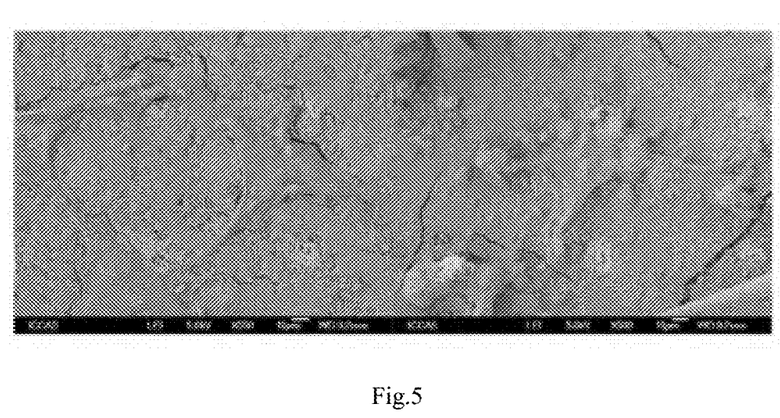
FIG. 5 is the SEM image of preosteoblast (MC3T3) that are cultured on the biological microscope slide for different periods.

2.2. Cell Adhesion Test:

After being grinded into powder, the Regesi regenerative medical material is pressed into tablet (the diameter is 13 mm and the thickness is 2 mm). The Regesi regenerative medical material tablet is subjected to sterilization and disinfection and put into 24 hole plate. Then the pre-osteoblast (MC3T3) is inoculated into 24 hole plate by $1\times10^4$ cells/mL, cultured for 1 d and 3 d. Then using 2.5%glutaraldehyde to fix for 24 hours at 4° C., washing with PBS for 3 times, gradient eluting with ethanol (50%, 75%, 95% and 100%), gold-plating after natural drying and observing with SEM, as shown in FIG. 5. The results show that an excellent attachment of osteoblasts on the surface of biological glasses and cells become longer after culturing for 1 day, wherein the filopodia occurs. After culturing for 3 days, cells become further extended and enlarged and the filopodia becomes more obvious. All these demonstrates that the Regesi regenerative medical material has excellent cell compatibility, which is helpful to the attachment of the cells on the surface of the Regesi regenerative medical material.

Figure 6:
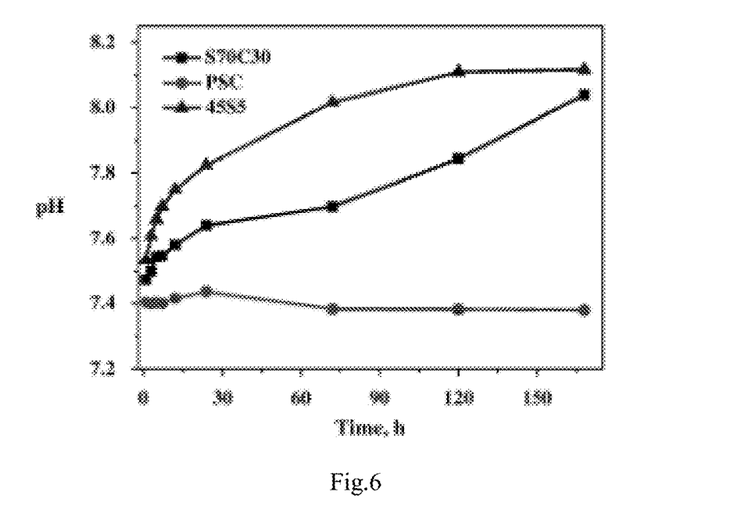
FIG. 6 shows pH value changes of the exemplary regenerative medical material sheet in the present invention in SBF solution.

3. Degradation Experiment:

Regesi regenerative medical material sheet (PSC, 45S5 and S70C30) is put into SBF solution to measure the changes of pH values thereof, the result is shown in FIG. 6. It can be seen from the figure that the pH values of samples of 45S5 and S70C30 (both are already reported products) both increase in the initial 168 hours while pH values of PSC samples (regenerative medical material in the present invention) keep constant during this period (~7.4, physiological pH value)), as shown in FIG. 6. The early researches show that the increase of pH values are not helpful to the growth of cells. Generally, for the test on the cellular compatibility of samples of 45S5 and S70C30, both samples need to be put into the phosphate buffer solution for immersion of 24 hours to remove some ions on the surface of sample and prevent them from killing cells. Due to the stable changes of pH values, generally PSC samples do not need pre-treatment and can be directly subjected to the cellular compatibility experiment. Besides, the above experiment results show that PSC possess excellent cellular compatibility, which is helpful to the adhesion, proliferation and differentiation of cells. These results show that PSC can be directly used in vivo after disinfection and sterilization.

Figure 7:
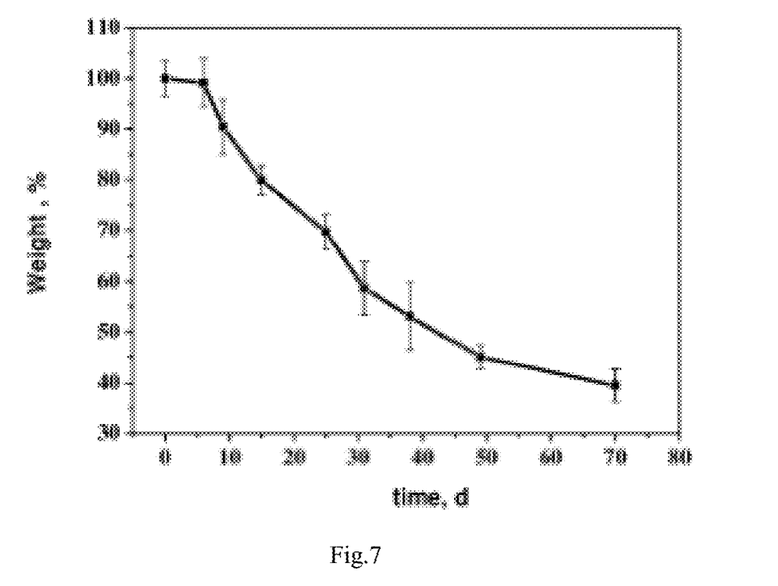
FIG. 7 shows the weight changes of the exemplary regenerative medical material in the present invention in water.

The Regesi regenerative medical material tablet is put into deionized water (5 tablets/50 ml) for degradation experiments, wherein the deionized water therein is completely replaced at each interval point-in-time. 5 tablets of samples are taken out and the water on the surface thereof are absorbed with paper. It is dried in a vacuum drier, weighed. The average value thereof is obtained, and the results are shown in FIG. 7. The results show that the materials start to degrade on the 6th day and the degradation becomes faster on the 9th day. The degradation can reach 40% of the original one on the 70th day and the degradation rate slows down.

The degradation experiments on the Regesi regenerative medical material is conducted in SBF solution. HA is formed on the surface of the material along with the release of ions in the material. It can be degraded to be ~80% of the original one in the initiate one month, but HA is entirely covered on the surface of the material, which causes the weight thereof don't change much, thus the degradation of the Regesi regenerative medical material is in accordance with the degradation rate under its in vivo metabolism. The degradation of the 45S5 biological glasses reported at present is investigated mainly by being implanted into body and the complete degradation needs 1-2 years.

Preclinical studies on the application of the Regesi regenerative medical material in the spinal and segmental bone defect repair.

1. Material Science

The Regesi biological active glasses are immersed in the simulated body fluid and changes of pH values are detected. The largest compressive strength in vitro is tested by the biological mechanical experiments. Micromorphology and surface contact angle of the material is observed with an electron microscope, the surface of the material is sprayed with gold films, and the surface morphology and microporous structure are scanned and observed.

2. Cytology

Regesi biologically active glasses, as the experimental group, and Gsk materials, selected as the control group (reference group), are added into the osteoblast culture solution mediums respectively. The influence of the material on the Type I collagen of osteoblast, osteocalcin and alkaline phosphatase gene expression of osteoblast is detected with the Real-time quantification PCR so as to further study the possible mechanism for the material to facilitate the proliferation of osteoblast. Meanwhile, the extracts of the above-mentioned two materials are used to culture the osteoblast. The cell growth curve is measured with MTT method and the relative growth rate RGR=(experimental group/control group)×100% is calculated according to 6 grade toxicity classification method and the toxicity ratings is conducted. The osteoblast is cultured in vitro and then respectively inoculated onto the above-mentioned two materials. The cell adhesion rate and cell adhesion force are measured, the adhesion rate=the amount of adherent cells/the total amount of cells×100%. The adhesion force of cells is measured with micropipette sucking method, and the observation is conducted by scanning electron microscopy. The experiment of compositing cells with materials is conducted by respectively putting materials of 1.0 cm×1.0 cm×0.5 cm size into the culture plate and inoculating the cell suspension onto the surface of the material to conduct the composite culture. The growth situation of cells on the surface of materials is observed in the inverted phase contrast microscope.

3. Animal Experiments 1) 60 male sheeps whose average weight is 75 kg are selected and divided into three groups with each group 20 sheeps. The Lumbar anterior lumbar 2 centrum resection is conducted under the condition of general anesthesia and sterility and the spinal segmental bone defect model is manufactured. Meanwhile, ulna middlepiece 4.5 cm bone and the periosteal defect model are manufactured. The cylindrical Regesi biological active glasses, Gsk materials and PMMA are respectively implanted into the gap and ulna defects position after centrum excision, and the three repair materials are respectively fixed onto the upper and lower centrums of the adjacent segments and the repair position of the ulnar bone defects. Bone healing and defect repair situations are observed by X-ray inspection on the ulna and lumbar adem position at the 1th, 6th and 12th weeks after surgery. Meanwhile, 5 animals in three observation groups are respectively executed and the titanium plate is removed with surgery. The adjacent centrum including the materials and the ulnas which are adjacent with the defect are taken out. The following studies are done: a. making sections, and observing the growth situation of newborn bones and degradation situation of the materials on the material filled part with a microscope; b. conducting the compression and tension strength of the biomechanics test samples; c. putting the sample into the Micro-CT system to conduct the three dimensional reconstruction observation and the mineral content (TMC) and bone volume fraction (BVF) of newborn bone tissues at the bones graft site are quantitatively analyzed with the Microview ABA software; d. the surplus materials after degradating and newborn bones within the bones graft area of each sample are shown compositely with different colors by Overlay method. The titanium plate for fixing centrum and ulna are taken from the remained 5 animals under the condition of general anesthesia and sterility at the 24th weeks after surgery and wound is closed. The movement of limbs and walking ability of the sheep are observed after surgery. Animals are executed at the $32^{nd}$ weeks after surgery and the samples of repaired centrum and ulna are taken out to do the corresponding biomechanics measurement and histological analysis.

2) 80 white rabbits of New Zealand are divided into a castrated group and a sham-operated group, there are 60 rabbits in the castrated group and 20 animals in the sham-operated group. The rabbit osteoporosis model is established by the bilateral ovarian castration method. The castrated group is divided into Regesi group, PMMA group and blank control group with each group 20 animals. The injectable Regesi biological active glasses can be injected into the L1, L2 centrum of Regesi group rabbits and PMMA is injected into the L1, L2 centrum of PMMA group rabbits by simulating vertebroplasty. 5 rabbits in each group are executed at the 1st, 6th, 12nd and 24th week after surgery. The corresponding centrum is taken out and the situation of newborn bone growth on the filled part and the material degradation are analyzed by histology, Micro CT analysis and microscope and the compressive strength and tensile strength of the Regesi biological active glasses are evaluated by the biomechanics experiments.

Figure 8:
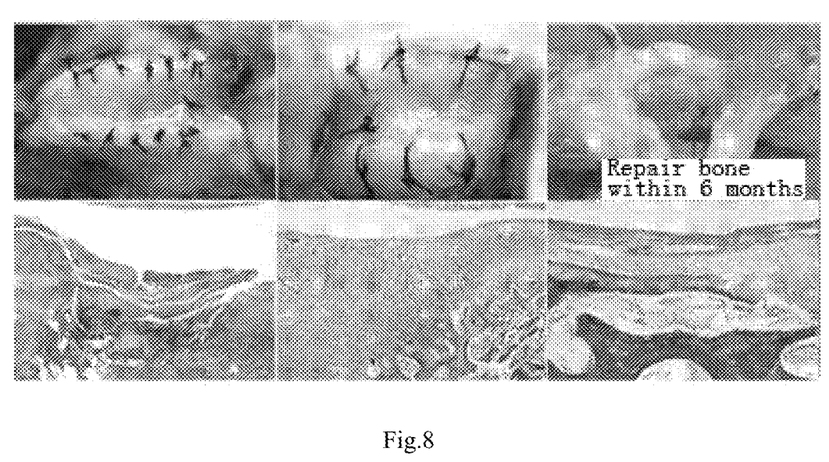
FIG. 8 shows the result map of applying the Regesi regenerative medical material to spinal and segmental bone defect repair.
Figure 9:
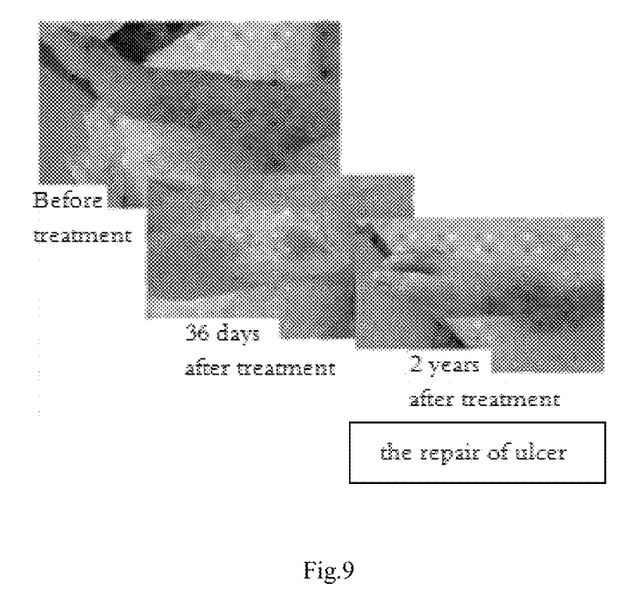
FIG. 9 is the image for the therapeutical effect of the developed ulcer repair material (gelatin) by adopting the Regesi regenerative medical material as the core.
Figure 10:
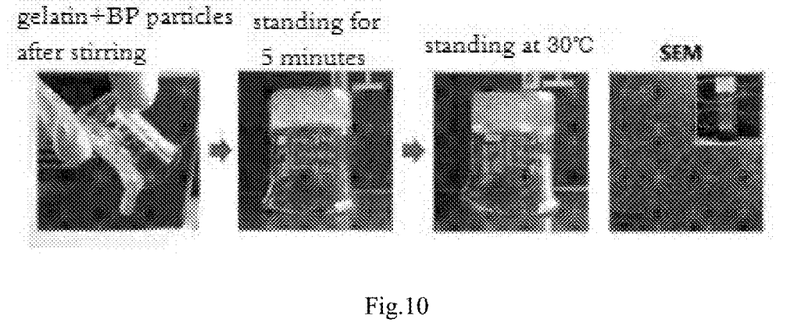
FIG. 10 is the experimental map showing that the Regesi regenerative medical material can be easily coated, which illustrates that the regenerative medical material in the present invention can be melted at the body surface temperature and form films.
Figure 11:
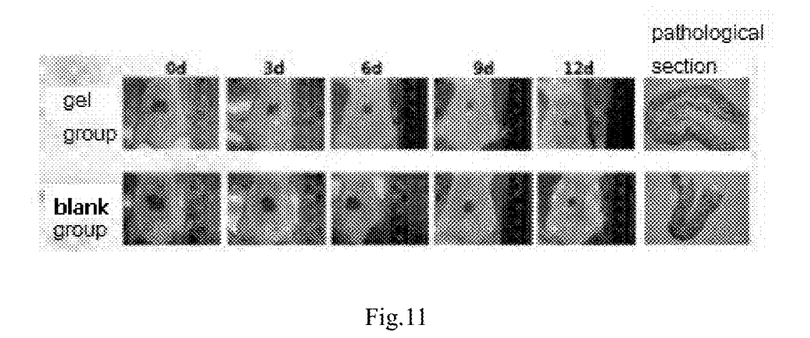
FIG. 11 is the experimental map showing the influence of the regenerative medical material on wound healing, which illustrates that the regenerative medical material in the present invention improves the speed and quality of wound healing and the hair follicle is produced.
Figure 12:
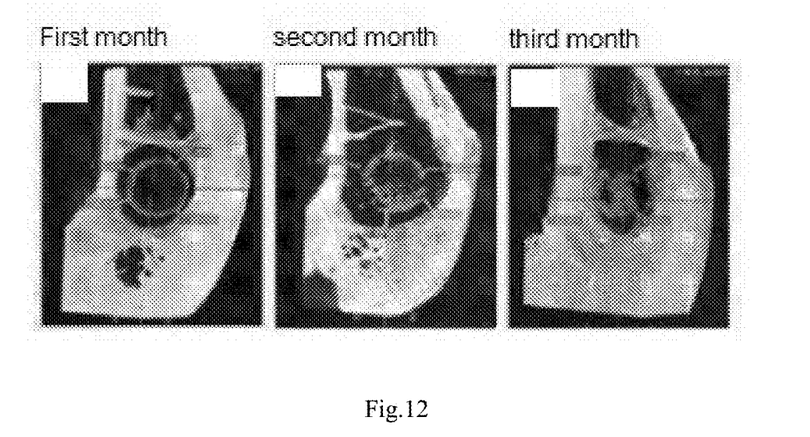
FIG. 12 is the map showing the regeneration of bone defect site when the regenerative medical material acts as the composite cancellous bone filler porous support, which shows that it is similar with the cancellous bone in the mechanical properties and the material in the present invention facilitates the regeneration of bones in the defect sites.
Figure 13:
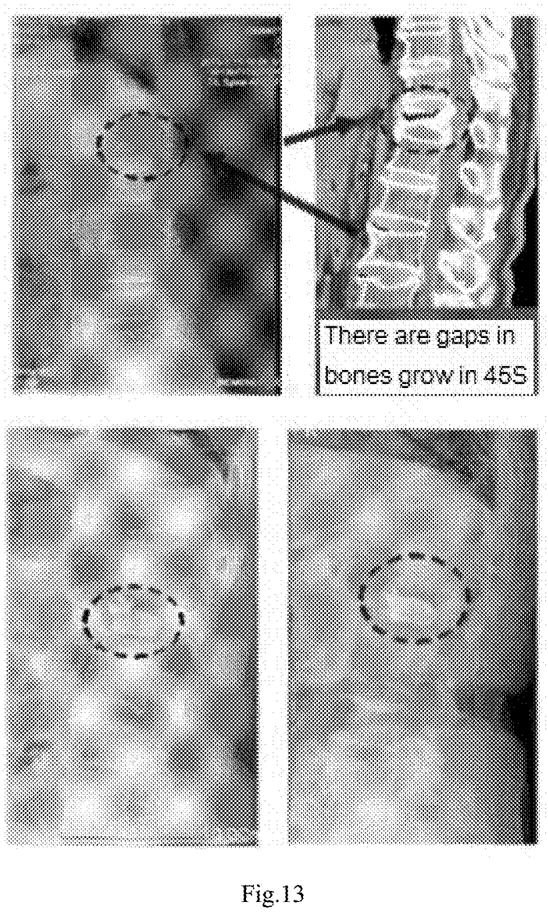
FIG. 13 shows the comparison for properties of the generated bones between the regenerative medical material in the present invention and 45S material as the control which shows that over fast for 45S degradation rate is easily to form bone collapse, and over strong for hardness is easily to cause periphery fracture.

With the above-mentioned experiments, the Regesi materials in the present invention are demonstrated to possess excellent compressive strength and tensile strength as well as the degradation situation etc (refer to FIG. 8 etc) compared with Gsk material group, PMMA group and blank control group.

Researches on the properties of existing biological active glasses.

The 45S powder samples are adopted as the measurement object.

The experimental process:

1) Sterilizing the 45S at high temperature and pressure

2) The preparation of leaching liquor: immersing the 45S which have been sterilized into the MEM culture medium with the corresponding volume for 24 hours at 37° C. The percentages of mass to volume are respectively 0.1%, 1%, 10%.

3) Taking the supernatant from the leaching liquor and the pH thereof is adjusted to 7.2 with 1M HCl, sterilizing with the 0.22 μm filter head, and then keeping at 4° C.

4) Leaching liquor of three concentrations are respectively added into 10% FBS.

5) The proliferation ability of Hacat cells is detected with CCK-8, and the absorbance-time curve is drawn.

Figure 14:
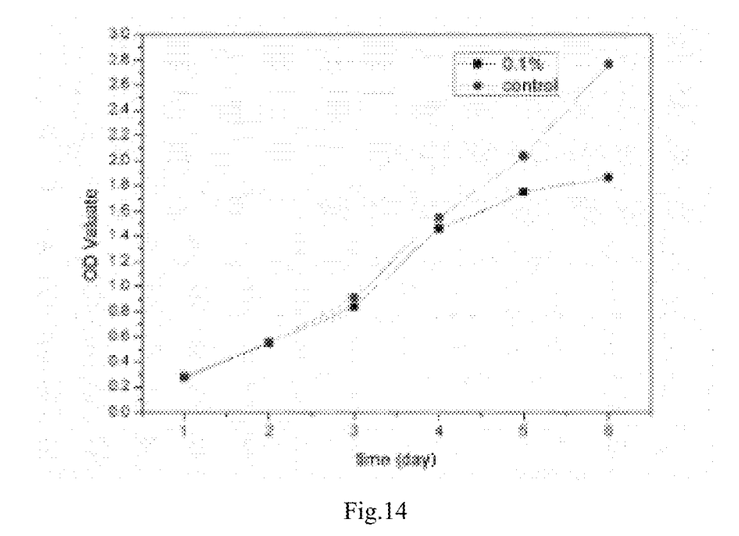
FIG. 14 shows the influence of 45S leaching liquor on Hacat cell proliferation.

Detection Results:

45S leaching liquor of 10% concentration is instable and massive floccule can be precipitated out in the storage process. The subsequent detection is not done. It is discovered that all cells are dead at the second day after adding leaching liquor of 1% concentration during the detection process of CCK-8. The leaching liquor of 0.1% concentration does not present obvious cytotoxicity to cells, but the cell growth in the late stage detection is slower than that of the control group, as can be known from FIG. 14.

Supplementary experiment (the influence of immersing 45S in the distilled water on pH values)

Experimental process: 45S is immersed in the distilled water according to 1% concentration of mass-volume ratio and pH values at different time points are tested.

Test Results:

| time | 0 h | 4 h | 7 h | 24 h |
|---|---|---|---|---|
| pH value | 9 | 10 | 11 | 13 |

Conclusions:

The results show that the pH value of 45S leaching liquor continuously increases as the leaching time increasing, and reaches 13 at the 24th hour. The sharply increase of pH value results that the strong cytotoxicity is shown in the CCK-8 test.

Other Experiments 1) 45S after sterilization at high temperature and high pressure is added into MEM culture medium. The volume percentage of 45S is respectively 0.1%, 1%, 10%. As soon as the 45S is added into MEM culture medium, obvious color changes occur, showing that the change of PH is very large. After being immersed for 24 hours, the supernatant is taken out and its pH value is adjusted to 7.2 with 1M HCl. As the concentration of 45S increases, the basicity of the culture medium becomes stronger and the amount of the demanded HCl becomes larger. In order to determine the experiment result, changes of pH values are detected after the 45S is immersed in the distilled water. The detection results still show that 45S causes great increase in pH and cytotoxcity generates.

Figure 15:
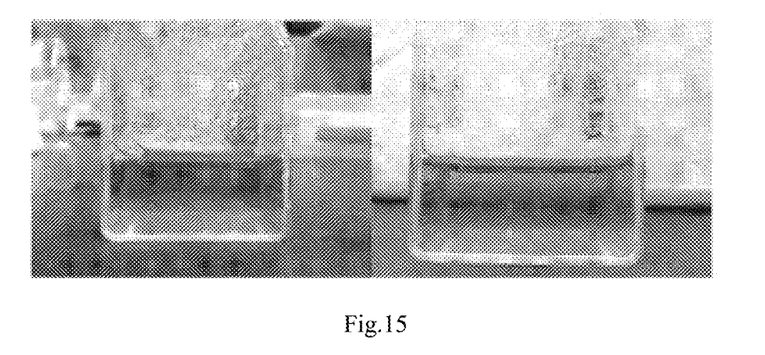
FIG. 15 is the image of the degradation experiment of 45S powder.

2) Taking the prepared 45S leaching solution taken out from the bridge at 4° C. and finding that massive white floccule is in the sample of 10% concentration, which does not dissolve in water bath for half hour at 37° C. This sample of this concentration is not subjected to the subsequent CCK-8 test. 45S powder of 10% concentration presents as sol in MEM after standing still for two weeks at room temperature, which demonstrates that the degradation rate of 45S powder is fast, as can be referred in FIG. 15.

3) During CCK-8 test process by adding FBS into leaching liquor of 0.1% and 1% concentration, it is discovered that the leaching liquor of 1% concentration presents great cytotoxicity and all cells are dead. The leaching liquor of 0.1% concentration presents smaller cytotoxicity.

INDUSTRIAL PRACTICABILITY

The regenerative medical material in the present invention can be used in biologic bone repair toothpaste, tissue engineering regeneration and wound repair medical materials and especially present great scientific value and meaning in aspects such as tissue engineering, oral mucosa, bone repair materials and wound repair. It will make great contributions in areas such as the tissue engineering and biotherapy.

Various improvements and changes can be made to the specific embodiments of the specification in the present invention under the condition that the scope or spirit of the present invention is not departed, which is obvious for a person skilled in the art. Other embodiments obtained from the specification of the present invention are obvious for a person skilled in the art and the description and embodiments in the present application are merely exemplary.

What is claimed is:

1. A regenerative medical material for promoting the repair of soft and hard tissue, characterized in that the regenerative medical material has three-dimensional network structure and is a composite material consisting of inorganics and organics, wherein,
   the mass ratio of the inorganics to the organics is 2:1-4:1;
   the inorganics contains 12-38% $SiO_2$, 3-5% $Na_2O$, 15-29% CaO, 10-32.5% $P_2O_5$, 1-5% inositol hexaphosphate, and 1-5% cyclohexanhexol phosphate, and a balance of impurities, with the content of impurities being less than 0.5% based on the total mass of the inorganics;
   the organics contains 30-60% carboxymethyl chitosan, and 30-60% sodium hyaluronate based on the total mass of the organics.

2. The regenerative medical material for promoting the repair of soft and hard tissues according to claim 1, wherein a weight ratio of calcium to phosphorus in the inorganics is in a range of 1.50 to 1.80.

3. The regenerative medical material for promoting the repair of soft and hard tissues according to claim 1, wherein a weight ratio of calcium to phosphorus in the inorganics is 1.67.

4. The regenerative medical material for promoting the repair of soft and hard tissues according to claim 1, a pH value thereof is 7.4±1.

5. The regenerative medical material for promoting the repair of soft and hard tissues according to claim 1, a degradation time in vivo thereof is in a range of 4 weeks to 12 weeks.

6. A method of preparing the regenerative medical material for promoting the repair of soft and hard tissues according to claim 1 wherein the method comprises the following steps:
   mixing soybean extract used as a phosphorus precursor, ethyl orthosilicate used as a silicon precursor, at least one of calcium nitrate tetrahydrate, calcium nitrate and calcium chloride used as a calcium precursor and water and/or ethanol used as reaction medium to prepare gelatin precursor sol solution, sintering the gelatin precursor sol solution at a constant temperature of 300~700° C. to obtain inorganics;
   mixing the inorganics with carboxymethyl chitosan and sodium hyaluronate, and heating to dissolve; wherein the preparation method of the soybean extract comprises: (1) smashing a soybean hull; (2) acid leaching a smashed material and filtering; (3) neutralizing a leach liquor with alkali; (4) precipitating and leaching a calcium salt (5) ion exchanging with RH+ resin; (6) evaporating and concentrating to obtain the soybean extract, wherein the content of hydroxyl phosphorus in the soybean extract is 40-60 mass %.

7. A cell growth carrier, characterized in that the cell growth carrier contains the regenerative medical material according to claim 1.

8. The regenerative medical material for promoting the repair of soft and hard tissues according to claim 1, wherein the mass ratio of the inorganics to the organics is 3:1.

9. The regenerative medical material for promoting the repair of soft and hard tissues according to claim 8, wherein a weight ratio of calcium to phosphorus in the inorganics is in a range of 1.50 to 1.80.

10. The regenerative medical material for promoting the repair of soft and hard tissues according to claim 8, wherein a weight ratio of calcium to phosphorus in the inorganics is 1.67.

11. The regenerative medical material for promoting the repair of soft and hard tissues according to claim 8, a pH value thereof is 7.4±1.

12. The regenerative medical material for promoting the repair of soft and hard tissues according to claim 8, a degradation time in vivo thereof is in a range of 4 weeks to 12 weeks.

* * * * *